US006829361B2

(12) United States Patent
Aarts

(10) Patent No.: US 6,829,361 B2
(45) Date of Patent: Dec. 7, 2004

(54) HEADPHONES WITH INTEGRATED MICROPHONES

(75) Inventor: Ronaldus Maria Aarts, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 550 days.

(21) Appl. No.: 09/739,513

(22) Filed: Dec. 18, 2000

(65) Prior Publication Data

US 2003/0190047 A1 Oct. 9, 2003

(30) Foreign Application Priority Data

Dec. 24, 1999 (EP) ........................................... 99204539

(51) Int. Cl.[7] ............................ H04R 5/00; H04R 5/02; A61F 11/06

(52) U.S. Cl. ........................ 381/309; 381/17; 381/71.6; 381/310

(58) Field of Search ................................ 381/309, 310, 381/71.6, 72, 17

(56) References Cited

U.S. PATENT DOCUMENTS 3,962,543 A 6/1976 Blauert et al. .............. 179/1 G
5,487,113 A * 1/1996 Mark et al. .................... 381/17
5,815,582 A * 9/1998 Claybaugh et al. ........ 381/71.6
6,021,205 A * 2/2000 Yamada et al. ............. 381/310
6,122,383 A * 9/2000 Berge ......................... 381/71.6
6,567,525 B1 * 5/2003 Sapiejewski ............... 381/71.6
6,597,792 B1 * 7/2003 Sapiejewski et al. ...... 381/71.6
6,625,287 B1 * 9/2003 Wurtz ........................ 381/94.1

FOREIGN PATENT DOCUMENTS

EP 0661906 A1 1/1991 ............. H04S/1/00
EP 0912075 A1 10/1997 ........... H04R/29/00

OTHER PUBLICATIONS

Patent Abstracts of Japan, vol. 1999, No. 05, May 31, 1999, JP 11032397 A.

* cited by examiner

*Primary Examiner*—Minsun Oh Harvey
*Assistant Examiner*—Laura A. Grier

(57) ABSTRACT

A sound reproduction system includes headphones (11). The headphones include structures for generating sound (4, 5) and microphones (6, 7). Further, the system includes filters (8,9) for filtering a signal such that the sound produced simulates external sound sources. The system includes a feed-back and control system (10) in which signals ($r_l(k)$, $r_r(k)$) from the microphones (6, 7) are used to set the settings $W_{XL}(k)$, $W_{XR}(k)$ of the filters (8,9).

8 Claims, 5 Drawing Sheets

HEADPHONES WITH INTEGRATED MICROPHONES

BACKGROUND OF THE INVENTION

1. Field of the Invention

The invention relates to a sound reproducing system comprising headphones with sound generating means and means for controlling the sound signal generated by said headphone sound generating means to simulate external sound sources.

The invention also relates to a headphone for a sound reproducing system.

2. Description of the Related Art

Headphones are used in and for audio equipment, such as (mobile) CD-players, but also in call-in centers.

The headphones comprise a means for generating sound (usually a small loudspeaker). A recorded sound signal (voice or music) is sent to the headphones) and sound generators inside the headphone generate a sound. The listener will, however, perceive the generated sound as being generated inside or very near the listener's head (which in fact it is), unless the sound signal is adapted. Such a sound is perceived to be unnatural. It is known to process the signals such that the perception of the sound signal by the listener is such that he/she believes to hear external sound sources, i.e., the listener perceives a more natural sound. To achieve this, the signals are processed through a filter set to alter the characteristics of the signal such that the sound generated near, or within, the head simulates an (or more than one) external sound source(s). An important aspect in this respect is the transfer characteristics of sound by an external source to the head and the pinnae of the ear itself, the so-called Head Related Transfer Function (HRTF), i.e., the manner in which sound becomes attenuated and altered by the head and pinnea itself before it actually is heard. Attempts to process the signals taking into account the HRTF to obtain external source simulation, are known from J. Acoust. Soc. Am. 85(2), pages 858–878, F. L. Wightman and D. Kistler, February 1989: 'Headphone simulation of free-field listening I and II'.

Such attempts, however, do not always prove to be successful. The HRTF is dependent on the actual shape and form of the head and the ear and differs substantially from one person to another. Furthermore, head movements complicate matters as they also influence the sound perception.

Japanese patent application JP 08/079,900 A discloses providing the headphones with measuring devices to measure the distance between the ears, the height of the head and head movements. Although such measurements can be used to improve the sound reproduction, the results leave room for improvement. The HTRF is a strongly individual one which can only be approximately determined using the result of such measurement. Likewise the effect of head movements can only be approximately determined.

SUMMARY OF THE INVENTION

It is an object of the invention to provide a sound system as described in the opening paragraph with improved sound reproduction.

To this end, the system is characterized in that the headphones are provided with microphones, and the means for controlling comprises, or is coupled to means for regulating the sound production by the headphone sound generating means such that a signal registered by the microphones is substantially zero when at least one external sound source is operative in response to a signal, and means for recording the results of said regulating to influence external source simulating sound generation in the headphones and/or means for regulating the sound production by the headphone sound generating means, such that the difference between a signal registered by the microphones and a known signal is substantially zero, and means for recording the results of said regulation to influence external sound simulating sound generation in the headphones.

Each headphone is provided with a microphone. The microphone, which is located near or preferably in the ear, registers the sound generated by the headphone sound generating means as well as, in one aspect of the invention, by the at least one external source. The system comprises means for regulating the sound production by the headphone sound generating means such that the microphone registers a substantially zero signal when, simultaneously, at least one external source, in response to a signal, and the headphone sound generating means are active. The headphone then generates a, as far as the human perception is concerned, same auditive signal but of opposite sign as the external source(s). The system includes means for recording the results of the regulation. Thereafter, when the external source(s) (is) are shut off, or removed altogether, the sound perceived by the listener is the same as that for the external sources. The signal registered by the microphone will be equivalent to that when only the source would be operative. The relation between a signal sent to the source, such as a loudspeaker, and the signal sent to the headphone sound generating means to simulate such an external source, is then known. The data from the above-mentioned regulation are used for regulation of the sound signal to the headphones in such manner that the external source is simulated.

The relation between a signal sent to an external source; a signal sent to the headphone sound generating means and a microphone signal are thus measured. Such measurement does, however, not only give the relation between signals a (external source signal) and b (equivalent headphone signal), but also between signals b (headphone signal) and c (microphone signal) and signals a (external source signal) and c (microphone signal). These known relations can also, or separately, be used in another aspect of the invention as follows.

Once, for a 'standard head' or, in fact, for any head, the relations between signals a, b and c have been established, it is not, in all circumstances, i.e., for other heads, necessary to make further use of an external source with signal a. It suffices to know (and this is known) the microphone signal c corresponding to a particular external source signal a to regulate headphone signal b, if needed. When the headphone sound generating means 'truly' (signal b) simulates an external source (signal a), a particular microphone signal (signal c) should be registered. This is the case on the 'standard head'. However, when the headphone is put on another head, the HRTF will be different and the same signal b sent to the headphone sound generating means will generate a microphone signal c' different from the particular microphone signal c because of the different HRTF. The system has means for regulating the signal b sent to the headphone sound generating means (to b') in such manner that signal c' is equal to signal c, for recording the regulation data, and for using the regulation data for further sound production to simulate external source(s).

It should be noted that while, in embodiments, the headphone sound generating means and the microphone will be often separate elements, in some embodiments, the headphone sound generating means (headphone loudspeakers) may double in function as the microphone, especially when such headphone sound generating means is placed inside the ear channel.

Preferably, the system also comprises means for storing the regulation data for a specific person.

This enables regulation data to be kept and coupled to a specific user. The next time this user uses the system, an incoming signal is filtered in the 'right' or at least 'nearly right' manner.

These and other objects of the invention will be apparent from and elucidated with reference to the embodiments described hereinafter.

The figures are schematic and not drawn on scale.

DESCRIPTION OF THE PREFERRED EMBODIMENTS

Figure 1:
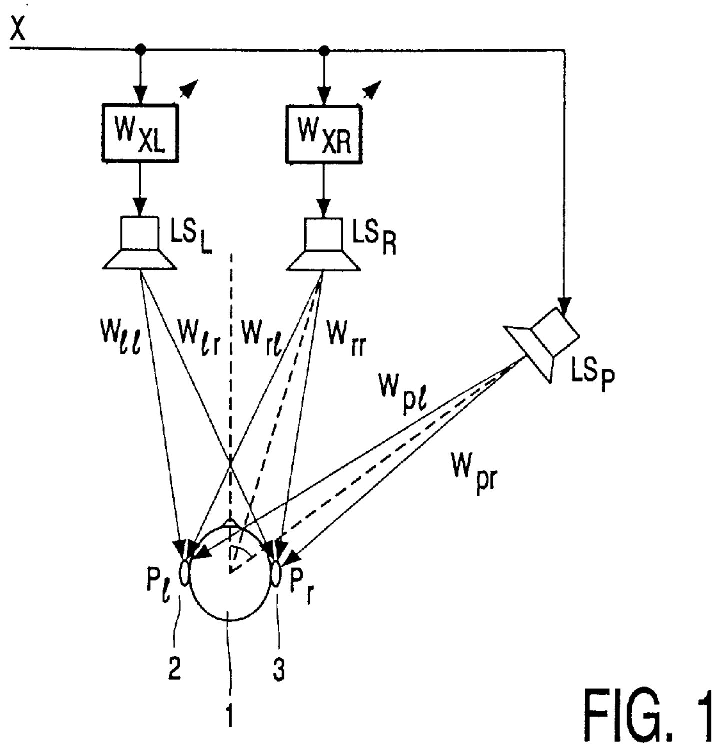
FIG. 1 illustrates, schematically, how to generate, from two real sound sources, a third so-called phantom source.

FIG. 1 shows a head of a person 1 with two ears 2 and 3. Two real loudspeakers $LS_l$ (loudspeaker-left) and $LS_r$ (loudspeaker-right) are present in a room. With these loudspeakers, it is meant to generate a sound as if a sound signal $V_r$ is generated by a loudspeaker $LS_p$ at some other point in space.

To calculate which signals have to be generated by the real loudspeakers $LS_l$ and $LS_r$ to give the person 1 the impression that the sound he/she hears is generated by a (phantom) sound source LSp generating a signal X, the signal X has to be altered, i.e., filtered by filter function $W_{XL}$(1 for left) for loudspeaker $LS_l$ and by $W_{XR}$ for loudspeaker $LS_R$.

Thus, the signal emitted by loudspeaker $LS_l$ is $XW_{XL}$, and the signal generated by $LS_R$ is $XW_{XR}$.

A signal generated by a sound source, be it real or phantom, causes (for real sources), or is supposed to cause (for phantom sources), at an ear, a pressure equivalent to the signal multiplied by a transfer function. The transfer function $W_{ll}$ (left loudspeaker to left ear), $W_{lr}$ (left loudspeaker to right ear), $W_{rl}$ (right loudspeaker to left ear), $W_{rr}$ (right loudspeaker to right ear), $W_{pl}$ (phantom loudspeaker to left ear) and $W_{pr}$ (phantom loudspeaker to right ear) are indicated in the figure.

The sound pressure $P_l$ at the left ear caused by loudspeakers $LS_l$ and $LS_r$ is the sum of the sound pressure $XW_{XL}$ (signal to left loudspeaker)+$W_{ll}$ (transfer function left loudspeaker to left ear)+$XW_{XR}$(signal to right loudspeaker)*$W_{rl}$ (transfer function right loudspeaker to right ear). Thus:

$$P_l=X(W_{XL}W_{ll}+W_{XR}W_{rl})$$

Likewise, the sound pressure $P_r$ at the right ear equals $$P_r=X(W_{XL}W_{lr}+W_{XR}W_{rr})$$

The sound pressure which would be caused by the phantom loudspeaker $$\text{(left ear)} \quad P'1 = XW_{p1}$$

$$\text{(right ear)} \quad P'r = XWpr$$

Substituting $P_l=P'_l$ and $P_r=P'_r$, leads to:

$$W_{XL}=(W_{pl}W_{ll}-W_{pr}W_{rl})/(W_{ll}W_{rr}-W_{lr}W_{rl})$$

$$W_{XR}=(W_{pl}W_{lr}-W_{pr}W_{rr})/(W_{lr}W_{rl}-W_{ll}W_{rr})$$

The filter functions, which, in this simplified model, have been described, actually have to be determined for each frequency, thus, actually, for each frequency, a filter function $W_{XR}$ and $W_{XL}$ has to be determined, fixed and used. With the proper filter functions $W_{XR}$ and $W_{XL}$, the listener hears the 'phantom source' $LS_p$. Thus, with two loudspeakers, a 'phantom' sound source at a sound can be generated which, to the listener, seems to come from another location than the actual location of the loudspeakers $LS_L$ and $LS_R$. This perception is dependent on the accuracy of the transfer functions (in this application sometimes also called 'filters' or 'filter settings') $W_{XL}$ and $W_{XR}$.

The filters $W_{XL}$ and $W_{XR}$ are difficult to determine because the transfer functions $W_{ll}$, $W_{lr}$, $W_{rr}$ and $W_{lr}$ from the loudspeakers $LS_l$ and $LS_r$ to the ear are difficult to determine. The transfer function for the real loudspeakers, to some extent, can be calculated and/or measured for a 'standard head', but, in reality, each head and each headphone is different, and thus, a transfer function is always more or less appropriate, but never really good. The transfer functions for the phantom source can only be estimated or theoretically derived. Especially for the higher frequencies, the transfer functions are difficult to determine because of the shape of the head and the ear canal. In short, the Head Related Transfer function, HRTF, is a highly individual one.

The transfer function needs to be calculated, and the calculation introduces errors.

For each frequency, the transfer function has to be determined, which either requires a large calculation effort and such calculation in itself may be a source of error, or necessitates the use of average transfer functions for a band of frequencies, which also introduces errors.

All transfer functions are, to some extent, dependent not just on the relative positions of the sound sources (real or phantom) and the ears, but also on other factors, such as objects near the sources or ears which may reflect or alter the sound waves, and thus, influence the transfer functions.

Thus, there is a need to improve the sound reproduction.

Figure 2:
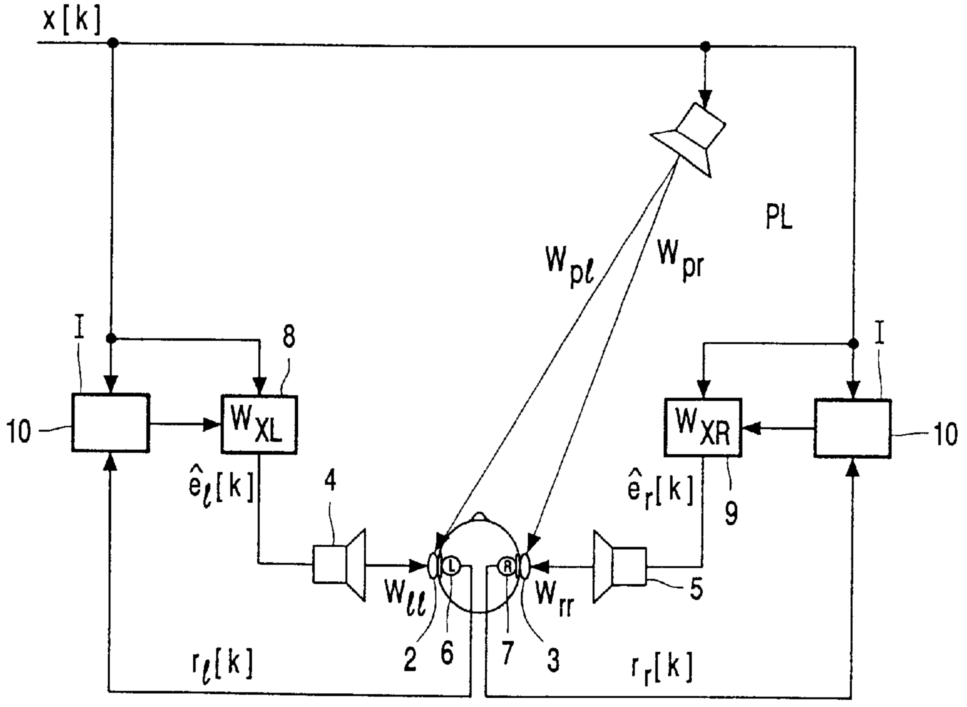
FIG. 2 illustrates, schematically, a system in accordance with the invention.

FIG. 2 illustrates a preferred embodiment of a system in accordance with the invention.

The system comprises two headphones each of which is provided with a microphone 6, 7. Each of the headphones has sound generating means 4, 5. A signal x(k) is relayed to the means 4, 5 through filter means (i.e., modulation means) 8, 9 having filter setting $W_{XL}$(k) and $W_{XR}$(k). In previous systems, the filters 8, 9 were fixed filters (as in FIG. 1) and thus, the settings $W_{XL}$(k) and $W_{XR}$(k) were fixed. These fixed filters were usually set to be equivalent to an 'average head' in an 'average room'. The signals after the filters are indicated with $\hat{e}_l(k)$ and $\hat{e}_r(k)$. The signals are $\hat{e}_l(k)=x(k)*W_{XL}(k)$ and $\hat{e}r(k)=x(k)*W_{XR}(k)$. In the system in accordance with the invention, microphones 6 and 7 are present in or near the headphones, and generate signals $r_l(k)$ and $r_r(k)$. The signals $r_1(k)$ and $r_2(k)$ result from the sum of the sound generated by the external source and the headphone. These signals $r_l(k)$ and $r_r(k)$ are fed to respective comparison and regulation means 10 which also have respective inputs for signal x(k) and respective outputs to filter means 8, 9 for adapting or regulating settings $W_{XL}(k)$ and $W_{XR}(k)$. It should be noted that in FIG. 2, only the transfer functions $W_{ll}$ and $W_{rr}$ are shown. This will be explained below.

A signal x(k) is supplied to the sound source PL and signals $\hat{e}_l(k)$ and $\hat{e}_r(k)$ are supplied to the sound generating means 4 and 5. The signals $r_l(k)$ and $r_r(k)$ are fed to the regulating means 10. This regulating means influences the settings of the filters $W_{XL}(k)$ and $W_{XR}(k)$ (and thereby the signals $\hat{e}_l(k)=x(k)*W_{XL}(k)$ and $\hat{e}_r(k)=x(k)*W_{XR}$ (k)) until the microphone signals $r_l(k)$ and $r_r(k)$ (and this preferably for each, or for a chosen set or selection of frequencies) become substantially zero. This may be done by a step-wise manner, i.e., one or more parameters (one or more of the settings $W_{XL}(k)$ or $W_{XR}(k)$) is (are) changed, it is then checked whether the signal $r_l(k)$ is increased or decreased, if it is increased, the parameter(s) is (are) changed in the opposite sense, if it is decreased, the parameter(s) is (are) changed in the same sense. This process is repeated until the signals $r_l(k)$ and $r_r(k)$ are substantially zero. For more details of such methods, reference is made to, e.g., 'Adaptive Filter Theory' by Simon Haykin, Prentice Hall, Upper Saddle River, ISBN 0-13-322760-X. It is to be noted that, in general, the less parameters have to be taken into account in such methods, the better the result is and the faster the result can be achieved. When the microphone signals $r_r(k)$ and $r_l(k)$ are substantially zero, the listener hears nothing. The resulting values for filter settings $W_{XL}(k)$ and $W_{XR}(k)$ are thereby determined. These filter settings can be, for instance, tables in a computer database. When the source PL is shut off or removed, the listener will hear a sound which, to the listener, is perceived to come from said source PL. Thus, the listener hears a 'phantom source' at the position of source PL. If the system is to be used for one person only, such tables could be the only one to use, but, preferably, the system comprises means (schematically indicated by input I in FIG. 2) for storing established settings $W_{XL}(k)$ and $W_{XR}(k)$ for the filters 8, 9, and matches the settings to data identifying the person. The next time that same person uses the system, the filter will then be set correctly, or at least nearly correctly, for that person, provided information identifying the person is given to the system. In practice, tables are, for instance, stored in a computer database matched with a name or number identifying the person.

Compared to previous methods and devices, the results are better and much more reliable, i.e., a much more 'natural' sounding and better 'localized' phantom source is heard by the listener. An advantage over fixed filters is that $W_{XL}$ and $W_{XR}$ can easily, faster and with much greater accuracy be determined and be adapted for different locations and for different persons. For instance, if head transfer functions are calculated with fixed filters, often parameters, such as, an average height and width of an average head, are used. Such parameters are sometimes useless or may even give clearly wrong results if the person in question is wearing some head ware, such as, a hat or, for instance, has a size head substantially different from the average head. Even the height of the person's hair may be of importance in this respect. Furthermore, more parameters than inter ear distance and head height may be of importance for the HRTF. The present invention does not suffer from these shortcomings but gives reliable results for each person, irrespective of the size and shape of the head and/or ear and/or whether said person wears a hat, because all of these factors do not play a role due to the microphone. Furthermore, the cross transfer functions ($W_{rl}$ and $W_{lr}$) are, due to the nearness of the source 4, 5 to the ear 2, 3, negligible or, in any case, very small. This enables, in preferred embodiments, as, e.g., shown in FIG. 2, to further greatly simplify the calculation, thus removing a source of error. In formula form, it holds:

$$W_{XL}=(W_{pl})/(W_{ll})$$

$$W_{XR}=(W_{pr})/(W_{rr})$$

These formulae are much simplified compared to formulae for phantom sound generation using loudspeakers with fixed filters. For each ear, the filter functions are only dependent on two, not six, transfer functions. In fact, the determinations of the filter settings $W_{XR}$ and $W_{XL}$ are independent. The measurement at the left (right) ear suffices to determine $W_{XL}(k)$ ($W_{XR}(k)$). This enables faster (less response time) and much better determination of $W_{XL}$ and $W_{XR}$. Furthermore, the response of the acoustic paths of the headphones is very short (thus further shortening response time). Furthermore, extraneous influences, such as, the shape of a room and objects in a room, on the transfer functions $W_{ll}$, $W_{rr}$ (and $W_{rl}$, $W_{lr}$) are not present in headphone sound reproduction. As a consequence, when tests were done with a system as schematically shown in FIG. 2 to see what the perceived difference would be between the real loudspeaker and a phantom loudspeaker, the location of the phantom loudspeaker was correct for both an anechoic room (a room in which sound reflection is reduced to a minimum) and a listening room (a room with normal sound reflection). These results were much better than those for known systems using fixed filters. As an alternative (and this may be in particular of importance for source at a relatively large distance) instead of working with a signal coming from each microphone, the sum ($r_l(k)+r_r(k)$) and difference ($r_l(k)-r_r(k)$) of these two signals could also be used. If the sum and the difference are zero, both signals are zero. Usually $W_{ll}$ and $W_{rr}$ are nearly equal (symmetric), and, at large distances from the source $W_{pl}$ and $W_{pr}$, are also not too much different. These facts are preferably used to simplify the calculations. It should be noted that in FIG. 2, the different filter means (8, 9) and regulation means (10) are drawn separately to increase clarity. They may be, and preferably are, all integrated in one device. In certain circumstances, for instance, a nearly symmetrically arranged fixed position of the source, only one microphone may be used. The data of said one microphone would then suffice.

Figure 3:
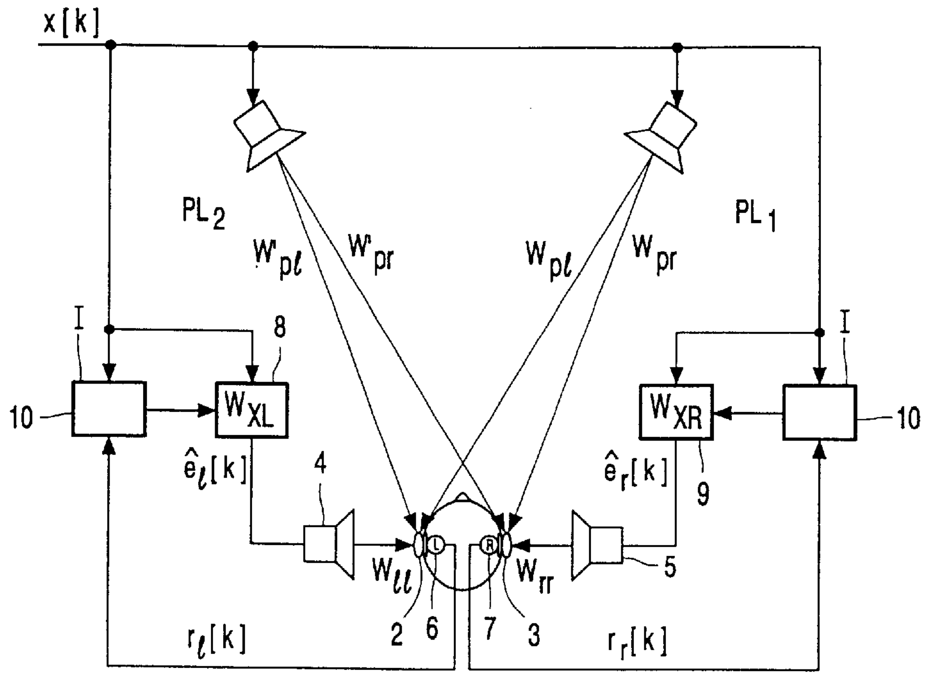
FIG. 3 illustrates, schematically, a further embodiment of a system in accordance with the invention.

FIG. 3 illustrates a further embodiment of a system in accordance with the invention. Two loudspeakers $PL_1$ and $PL_2$ are used. For both loudspeakers, the transfer functions $W_{XL}$ and $W_{XR}$ can be determined in the manner as described above. This can be done in the following manner. First, loudspeaker $PL_1$ is activated and microphone signals are made zero. The filter settings $W_{XL}(k)$ and $W_{XR}(k)$ for said loudspeaker are determined. Thereafter, loudspeaker $PL_1$ is deactivated and loudspeaker $PL_2$ is activated to determine filter settings $W'_{XL}(k)$ and $W'_{XR}(k)$ for loudspeaker $PL_2$. The filter functions for both loudspeakers having been determined, the system is capable of reproducing any mix of the two sound sources $PL_1$ and $PL_2$ with a very natural sound, i.e., stereo sound.

For a signal x(k) sent to loudspeaker $PL_1$ and, simultaneously, a signal y(k) sent to loudspeaker $PL_2$, the signals to the headphone sound generating means are:

$$\hat{e}_l(k)=x(k)*W_{XL}(k)+y(k)*W'_{XL}(k) \text{ and}$$

$$\hat{e}_r(k)=x(k)*W_{XR}(k)+y(k)*W_{XL}(k).$$

When more than two sources are to be simulated, the signals to the more than two sources could, for instance, be written as a vector and the filter settings for the different sources could be written in matrix form. Multiplication of the vector (for the sources) with the matrix (for the settings) will generate the signals $\hat{e}_l$(k) and êr(k). The matrix itself is determined by measurements and may be different for different persons and different rooms.

Figure 4:
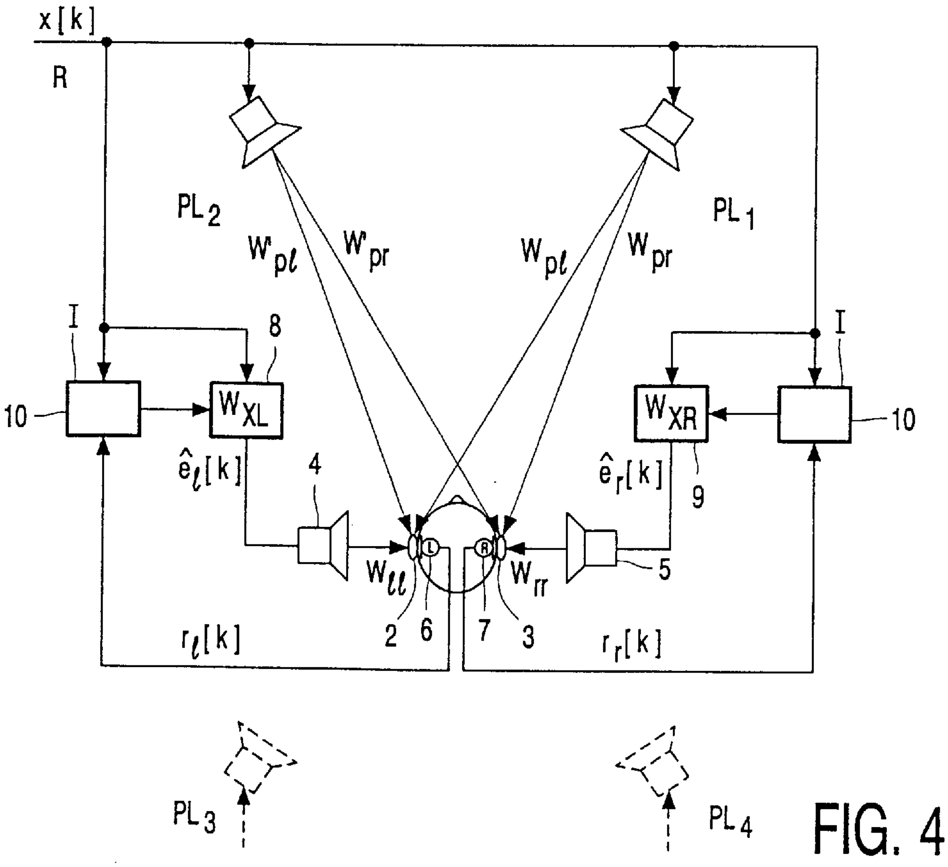
FIG. 4 illustrates yet a further embodiment of a system in accordance with the invention.

A further embodiment of the system in accordance with the invention is shown in FIG. 4. Having established the transfer functions $W_{XL}$ and $W_{XR}$, respectively, $W'_{XL}$ and $W'_{XR}$ for two loudspeakers $PL_1$ and $PL_2$, this knowledge can be used to 'create' using, for instance, geometrical principles more phantom sound sources, for instance, phantom loudspeakers $PL_3$ and $PL_4$. Using, for instance, thereafter, the above technique of vector-matrix multiplication, a 'surround sound' may be created. The problem with trying to do so using fixed filters lies, as already explained, among others, in the very individual Head Related Transfer Functions and also from local circumstances, such as, reverberation in a room. Starting from two known sources, one can, using geometry and/or standard techniques, calculate the transfer function for the phantom sources $PL_3$ and $PL_4$ in so far as geometry is concerned but not or much less the other influences. In a system in accordance with the invention, said difficulty is resolved for the main part, since use is made of actual measurements on an actual head with actual headphones (thus, taking into account the relevant HRTF) and in an actual room (thus at least partly taking into account the reverberation in the room) resulting in transfer functions which take these influences in account giving much better rendition of phantom sources.

Figure 5:
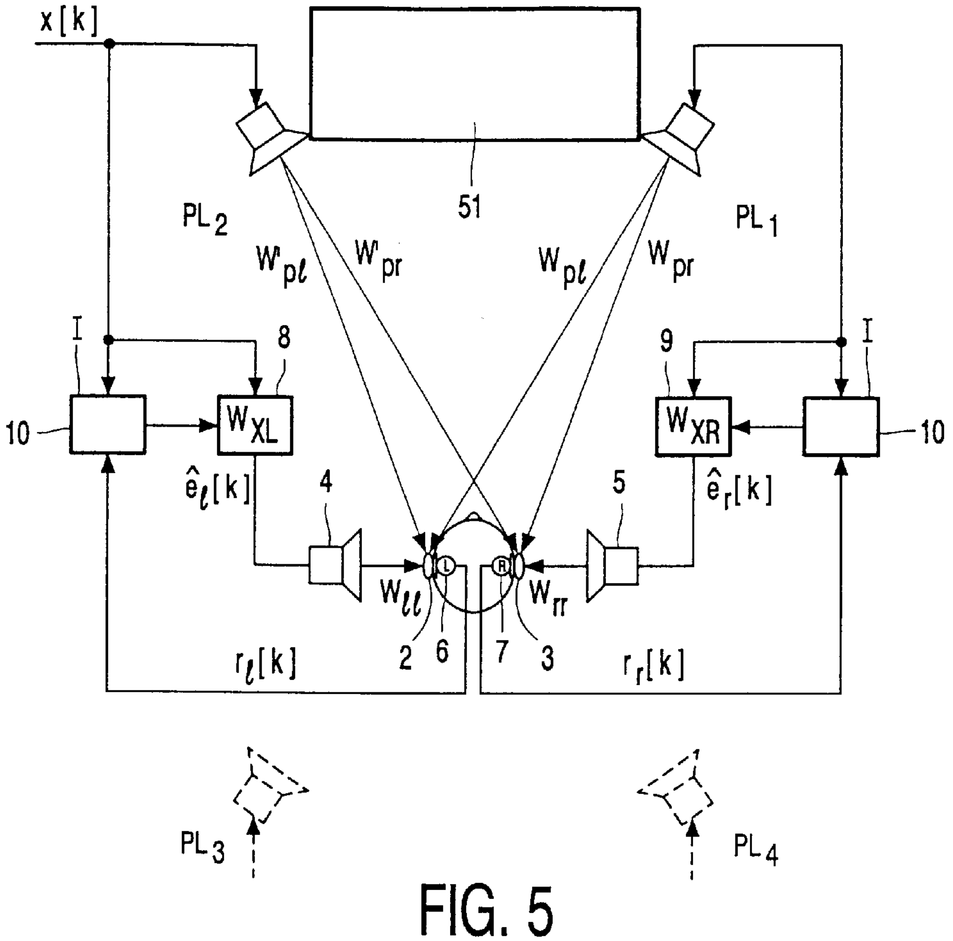
FIG. 5 illustrates a still further embodiment of a system in accordance with the invention.

A yet further embodiment is shown in FIG. 5. The headphones (or at least one of them, or the connection between the headphones) comprise means for measuring the position with respect to the two sources $PL_1$ and $PL_2$ and/or some fixed reference point. Such means can be, for instance, infra-red sources which are sensed by sensors in or near the sources $PL_1$ and $PL_2$ or infra-red sources in or near $PL_1$ and $PL_2$ which are sensed by sensors in the headphones. Such means may also comprise means for generating and sensing ultra-sound. In this example, the two 'real' loudspeakers are positioned at either side of a television set 51. Near or at least at one headphone, an emitter of a signal or sensor for localization signals is present and a stationary part of the system comprises a sensor or emitter for localization signals.

As explained before, the transfer functions are determined using the microphones 6 and 7 and when the two sources $PL_1$ and $PL_2$ are turned off, they are then audible in the headphones as 'phantom sources'. The transfer functions to simulate these two external sources $PL_1$ and $PL_2$ then include the individual HRTF and room-related factors. Knowing the position of the head and the filter, using geometric considerations, one or more phantom sources $PL_3$ and $PL_4$ can be created, or alternatively or in addition, the system may comprise tables with many transfer functions for many different positions of the listener vis-a-vis the sources. As the listener moves in the room, the position of the head vis-a-vis the sources $PL_1$ and $PL_2$ is regularly measured and used to create phantom sources $PL_1$ to $PL_4$ at the right places. The 'proper' filter functions may then be established either by, for instance, choosing a filter setting table associated with a position most nearest to the actual position or taking some average (for instance, by interpolation) of several filter settings corresponding to several positions close to the actual position. In establishing the 'proper filter functions' for real or phantom sources, use may be made of the fact that human ear is much more perceptible to sound coming from positions in front of the head, than to the back of the head. In other words, to create a 'surround sound', it is not necessary to have a number of sources equally distributed around the listener, i.e., the number of sources to the back of the head may be less.

The examples given so far all start with determining filter functions $W_{XL}$ and $W_{XR}$ for one or more loudspeakers (or channels) phantom or real by regulating the signal $\hat{e}_l$(k), $\hat{e}_r$(k) sent to the headphone sound generating means 4, 5 such that the signal $r_l$(k), $r_r$(k) measured by the microphone (s) is substantially zero when a signal x(k) is sent to a source $PL_1$, $PL_2$ and extracting filter setting data $W_{XR}$(k), $W_{XL}$(k) from said measurement.

Figure 6:
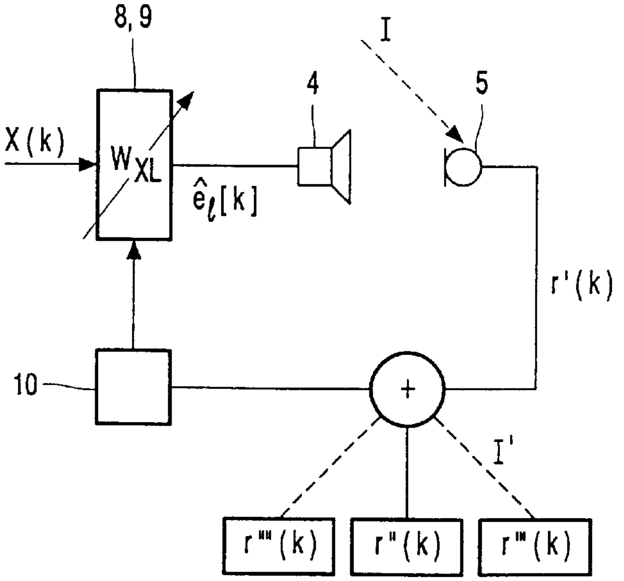
FIG. 6 illustrates another aspect of the invention.

FIG. 6 illustrates a different aspect of the invention. In this particular aspect, an external source has been used to find the filter settings $W_{XL}$ and $W_{XR}$ for a particular head, which, for simplicity, will be called a 'standard head'. These filter settings are, however, as explained, dependent on the very individual HRTF. For other persons, these settings may not be correct. As explained above, one way of overcoming this problem is to measure the filter functions for any individual person and store the filter function setting coupled with data identifying said person. However, although such procedure gives excellent results, this is a rather complicated procedure. In an aspect of the invention, a different route is followed. When the filter settings for a 'standard head' are correct (i.e., the microphone signal due to the sum of the sound of an external source and the microphone sound generating means due to a signal x(k) is zero), the external source is shut off, and a microphone signal r''(k) due to signal sent to the headphone sound generating means is measured (or alternatively the headphone sound generating means are shut off and the microphone signal due to the external source is measured). Data corresponding to the signal r''(k) are stored in the system. When another person puts on the headphones, the very same signal x(k) will generate with the same filter setting the same signal $\hat{e}_l$(k) sent to the headphone sound generating means 4, but a microphone signal r'(k) which differs, due to a difference in HRTF, from the stored signal r''(k). In FIG. 6, it is schematically illustrated that the system, in this aspect of the invention, comprises means for comparing the signal r'(k) to the signal r''(k) and means 10 for changing the filter settings $W_{XL}$(k) and $W_{XR}$(k) (the latter not being shown, for simplicity) such that a comparison between a signal registered by the microphones (r'(k)) and a known or calculated signal (r''(k), r'''(k), r''''(k)) show said two signals to be substantially the same. A comparison of the signals or data representing the signal r'(k) and r''(k) then shows that the signals are substantially the same. Such a comparison can be done in different ways. The most simplest is to store data for r'(k) and to calculate the sum or difference (depending on the sign of the stored data) of the data for r'(k) and r''(k). These data may directly represent the signal r'(k) and r''(k) or be some data derived from the signals, such derivation being done to reduce the data needed for comparison. For instance, the signals r'(k) and r''(k) may be converted into Fourier space and the comparison may be done in Fourier space. The filter settings are then recorded (for instance, in means 8, 9 or 10, but they could also be recorded in some other means) and they are used for further sound production to simulate an or more external source(s). It should be noted that, apart from the shape and size of the head, also other factors may be of importance, for instance, the acoustics (reverberations, for instance) of the site at which the sound was generated. In FIG. 6, r"(k) may, for instance, correspond to sound reproduction in a concert hall, r'"(k) to sound reproduction in a stadium, and r""(k) to sound reproduction in a small room (chamber or club). The user of the system may choose such settings, to his/her liking. In this example, the comparison signal r"(k) etc. are fixed signals corresponding with fixed situations. In a more sophisticated system, the comparison signal could be more freely chosen, for instance, by giving the user the opportunity to change the size and acoustic characteristics of the virtual site or the position of the listener within the site. The basic idea is that the signal r'(k) (and such for each channel) is compared to a stored or computer-generated signal (be it r"(k), r'"(k), r""(k)) and that the two signals are made substantially the same by changing the filter settings $W_{XR}(k)$, $W_{XL}(k)$.

FIGS. 7A to 7E illustrate several embodiments of a headphone for a system in accordance with the invention.

Figure 7A:
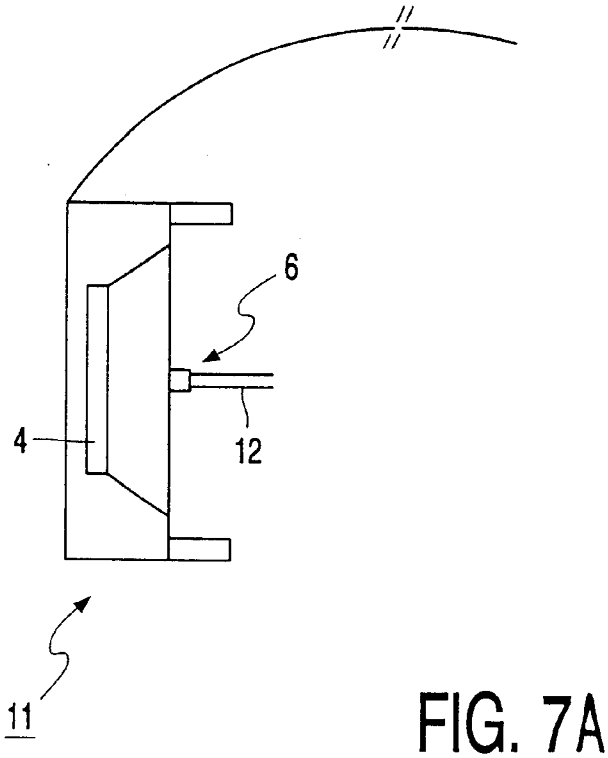
FIGS. 7A to 7E illustrate several embodiments of a headphone for a system in accordance with the invention.
Figure 7B:
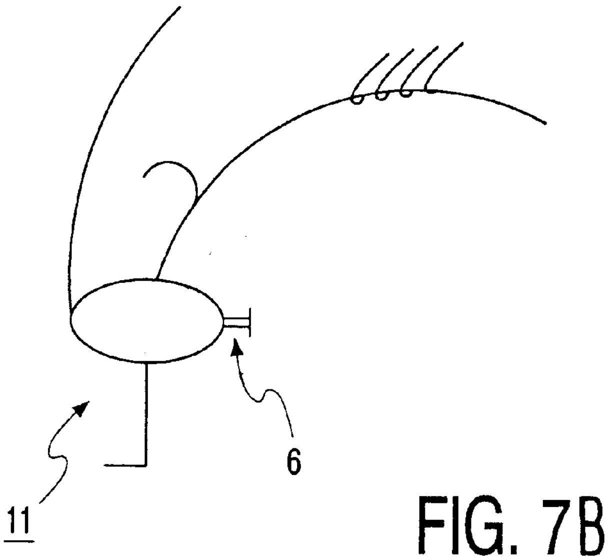
Figure 7C:
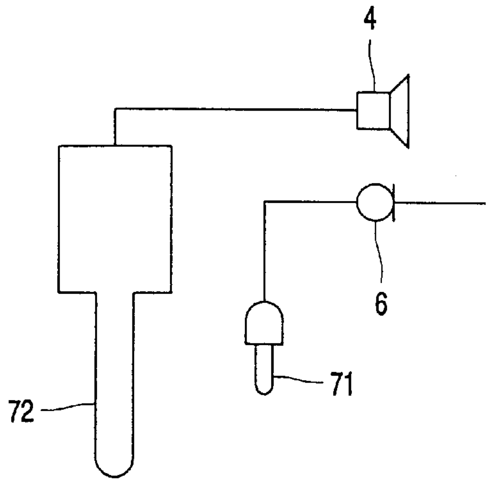
Figure 7E:
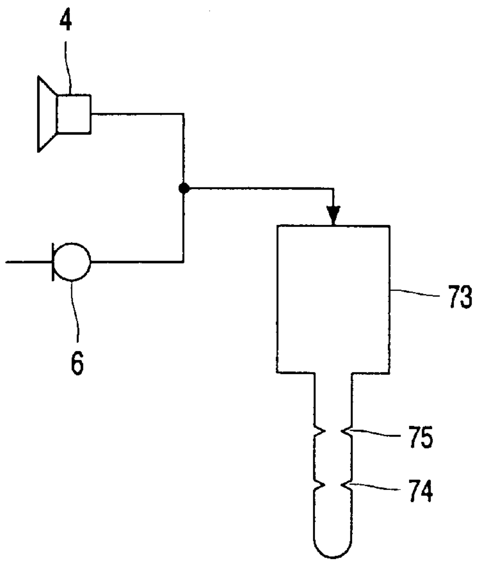

In FIG. 7A, a tube 12 is attached to the microphone 6 of headphone 11, the tube 12 being inserted in the inner ear. In this embodiment, in which the headphone 11 has a shell-like construction with the sound generating means inside the shell, it is preferred that the microphone registers the sound in the inner ear near the eardrum. For this purpose, the tubes 12, as sound guides, are provided. In FIG. 7B, the headphone is placed inside the ear and the microphone 6 near or in the inner ear. In FIG. 7C, the headphone 11 and microphone 6 are separate devices but both placed in or near the ear. The output signal of the sound generating means is fed to a jack 72, the output signal of the microphone is fed to a separate jack 71. In FIG. 7E, both output signals are fed to a single jack 73 which has two separate ports 75 and 76 through which the signals may be transferred to a part of the system. This embodiment is the most preferred embodiment, because one single jack is necessary. The part of the sound system in which the jack will be inserted may be provided with means for picking up the signals. Such a jack can be a standard jack, but for the extra output, likewise, the part of the sound system in which the jack will be inserted may be standard, but for the possibility of registering the signal from the microphone. This enables 'standard' equipment, at least as far as the user is concerned, to be used. The sound system will be able to operate with 'normal headphone' (in which case there will be no microphone signal), but will be able to register whether or not a headphone in accordance with a system of the invention is used, and if so, operate in accordance with the invention.

Figure 7D:
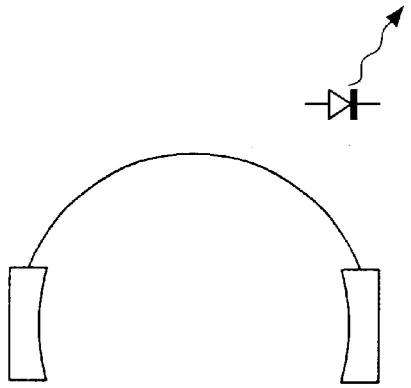

FIG. 7D illustrates that the signal ($r_l(k)$, $r_r(k)$ or any combination of derivative of or data representing said signals) from the microphone can be relayed wirelessly as well as by a separate plug.

It will be clear that within the framework of the invention, many variations are possible.

Figure 8:
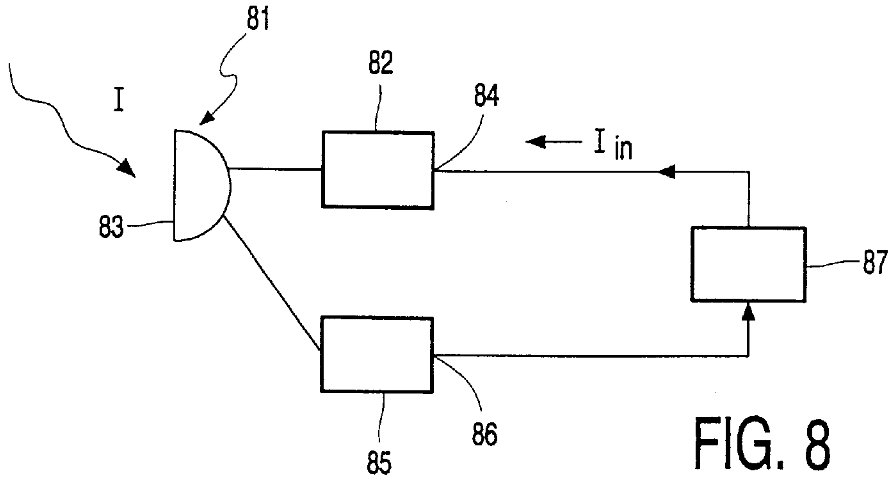
FIG. 8 illustrates, schematically, how the headphone sound generating means may be also the microphone.

For instance, in the above given examples, the microphone is shown as an element separate from the other elements. In other embodiments, the headphone sound generating means may itself be used as microphone. FIG. 8 illustrates very schematically how this can be done. Headphone sound generating means 81 comprises or is coupled to or with a means 82 for driving a membrane 83 to generate sounds. Said system is supplied with a signal $I_{in}$ via an input 84. The headphone sound generating means also comprises means 85 (which may have some, most or even all building elements common to means 82) with an output 86 which generates a signal $I_{out}$ corresponding to the movement of the membrane. A means 87 for regulating the signal $I_{in}$ has an input for signal $I_{out}$ and regulates $I_{in}$ such that $I_{out}$ becomes substantially zero when an external source generates a sound I. In these circumstances, the sound pressure at the position of the membrane is zero; thus it is silent. Preferably, for these embodiments, i.e., for the embodiments wherein the headphone sound generating means double in function as microphones, the headphone sound generating means are, in operation, located inside the ear.

In short; the invention can be described as follows:

A sound reproduction system comprises headphones (11). Said headphones comprise means for generating sound (4, 5) and microphones (6, 7) (i.e., means for recording sound). Further, the system comprises filter means (8, 9) for filtering a signal such that the sound produced simulates external sound sources. These filter means comprise filter setting date $W_{XR}(k)$, $W_{XL}(k)$. The system comprises a feed-back and control system (10) in which signals ($r_l(k)$, $r_r(k)$) from the microphones (6, 7) are used to set the settings $W_{XL}(k)$, $W_{XR}(k)$ of the filter means (8, 9). The signals can be used by making them zero (when an external source is used) ($r_l(k)=0$, see FIG. 3) or by comparing the microphone signals and a gauge signal zero ($r''(k)-r'(k)=0$, see FIG. 6) such that the two are substantially the same.

It should be noted that systems are known, for instance, for use in very high noise environments, such as airports, to cancel noise. In some of such systems, a microphone inside the headphone is used. The headphone sound generating means make a counter-noise to cut out or at least strongly reduce all noise within a certain frequency bandwidth. The idea behind such systems is that by eliminating the usually low frequency noise, the noise to signal ratio between the noise and the usually more high frequency communication sounds signals is increased. Such systems, however, do not simulate external sources nor are the microphone signals used to set filter settings.

What is claimed is:

1. A sound reproducing system including at least one external sound source, headphones and means for generating an input sound signal for said at least one external sound source and said headphones, said headphones comprising:

sound generating means for receiving said input sound signal; and means for controlling an output signal generated by said sound generating means for simulating external sound sources, characterized in that said controlling means comprises:

a microphone positioned in close proximity to said sound generating means, said microphone receiving a first sound signal from said sound generating means and a second sound signal from said external sound source, said microphone generating a resultant signal;

means for modifying the input sound signal applied to said sound generating means;

means coupled to receive said resultant signal for adjusting said modifying means until said resultant signal is substantially zero, whereby the user of the headphones hears nothing;

means for recording settings of said adjusting means; and means for applying said input sound signal to said at least one external sound source during a set-up mode while said adjusting means adjusts said modifying means, and for removing said input sound signal from said at least one external sound source and for causing said adjusting means to use said recorded settings during a operating mode, whereby in said operating mode, a user or the headphones perceives a phantom sound source corresponding to said at least one external sound source.

2. The sound reproducing system as claimed in claim 1, characterized in that the headphone is provided with a sound transporting means for transporting said first and second sound signals to said microphone.

3. The sound reproducing system as claimed in claim 2, characterized in that the sound transporting means comprises a tube for insertion in an ear of a user.

4. The sound reproducing system as claimed in claim 1, characterized in that the microphone is integrated in a headphone insertable inside the ear.

5. The sound reproducing system as claimed in claim 1, characterized in that the headphone sound generating means is also used as said microphone.

6. The sound reproducing system as claimed in claim 1, characterized in that the system comprises means for establishing a relative position of the headphones and a stationary element of the system.

7. The sound reproducing system as claimed in claim 6, characterized in that an emitter of a signal or sensor for localizing signals is positioned near or at least at one headphone, and the fixed part comprises a sensor or emitter, respectively, for localizing signals.

8. The sound reproducing system as claimed in claim 1, wherein said controlling means further comprises:

means for generating a known signal for said input sound signal;

means for measuring and recording data corresponding to the resultant signal in said operating mode when said headphone is placed on a standard head;

means for comparing said recorded data with data corresponding to an actual resultant signal when said headphone is placed on a user's head; and means for further adjusting said modifying means until said data corresponding to said actual resultant signal equals said recorded data.

* * * * *